_United States Patent_ [19]

Mee

[11] Patent Number: 5,073,503

[45] Date of Patent: Dec. 17, 1991

[54] BIOTHERMOGRAPHIC ANALYSIS OF PLANTS

[76] Inventor: John M. Mee, P.O. Box 25896, Honolulu, Hi. 96825

[21] Appl. No.: 378,458

[22] Filed: Jul. 12, 1989

Related U.S. Application Data

[63] Continuation-in-part of Ser. No. 792,564, Oct. 29, 1985, abandoned.

[51] Int. Cl.⁵ ............................................. G01N 25/20
[52] U.S. Cl. ........................................ 436/147; 47/58; 47/DIG. 1; 73/865.6
[58] Field of Search ............... 436/147; 435/29; 47/58, 47/DIG. 1; 73/865.6

[56] References Cited

FOREIGN PATENT DOCUMENTS

| | | | |
|---|---|---|---|
| 0628850 | 10/1978 | U.S.S.R. | 47/DIG. 1 |
| 0660631 | 5/1979 | U.S.S.R. | 47/DIG. 1 |
| 1183023 | 10/1985 | U.S.S.R. | 47/DIG. 1 |
| 1187765 | 10/1985 | U.S.S.R. | 47/DIG. 1 |
| 1311672 | 5/1987 | U.S.S.R. | 47/DIG. 1 |
| 1424762 | 9/1988 | U.S.S.R. | |
| 1433438 | 10/1988 | U.S.S.R. | 47/DIG. 1 |

OTHER PUBLICATIONS

Cunningham, "Microcalorimetry of Seed Germination," Master's Thesis, Chelsea College, Univ. of London (1978).
Prat, "Microcalorimetric Studies of Germination of Cereals," Can. J. Bot. 30:379–394 (1952).
Abstracts from American Society of Agronomy Annual Meeting, p. 100 (1985).
Enright, "Test Tells Good Seed from Bad", _Gaithersburg Gazette_, Jan. 8, 1986.
Mee et al., "The Calibration and Determination of Gross Energy in Hawaiian Cane Molasses", _Nutrition Reports International_, vol. 11, No. 4, pp. 323–326 (Apr., 1975).

_Primary Examiner_—David L. Lacey
_Assistant Examiner_—Jeffrey R. Snay
_Attorney, Agent, or Firm_—Larson & Taylor

[57] ABSTRACT

A method of biothermographically screening plants for favorable genetic characteristics such as drought resistance or heat tolerance is provided which comprises the nondestructive laboratory measurement of heat production of the plant sample or viable part thereof in a microcalorimeter under a given set of environmental conditions, and then using the measured heat production to assess the plant sample's potential reaction in the wild to those same conditions. The biothermographic analysis of the present invention represents a rapid, nondestructive way of predicting potential biological or economical yield under a variety of environmental field conditions, and can be conducted in a simple and inexpensive manner so as to particularly benefit those in the fields of agricultural biotechnology, plant genetics, and crop management.

4 Claims, No Drawings

BIOTHERMOGRAPHIC ANALYSIS OF PLANTS

This application is a continuation-in-part of application Ser. No. 792,564 filed Oct. 29, 1985, now abandoned.

FIELD OF THE INVENTION

The invention relates in general to a system of laboratory monitoring techniques for detection, identification, and characterization of genetic expressions in plants, and in particular to a method of biothermographically screening plants for favorable genetic characteristics under specific environmental conditions which will benefit crop productivity and breeding.

BACKGROUND OF THE INVENTION

Genetic variation forms the basis of all physical, chemical and biological diversity in plant and animal species. Natural and modified gene expressions are complex biological processes that can be observed for species over a wide range of environmental conditions. In plant agriculture, traditional field screening techniques which have been used for identifying germplasm accession and breeding lines are often based on field reactions to environmental stresses, as observed by way of crossing, hybridization, varietal separation, collection, and further testing. Unfortunately, the most commonly used field methods are usually labor intensive, as well as time consuming and expensive to carry out. In many cases, field trial data have lacked repeatability and have usually been inconclusive due to the varying environmental influences of different locations and different growing seasons.

Technological advances in molecular genetics can potentially provide new inroads to understanding genetic variance, and efficient ways of employing this knowledge can increase crop production. Crop improvement through tissue culture, leaf protoplast asexual reproduction, and even reproduction of DNA through cloning of plant cell nuclei all appear feasible given the current technological advances in this field. However, it is still the case that characterization of specific genetic attributes of particular plants and plant systems under stressed environmental conditions, as well as studies on the inheritability of particular traits, have been particularly difficult to carry out.

One physical parameter which can be studied quite readily is respiration, i.e., the exchange of gases, oxidation of organic molecules, etc. One instrument useful for measuring gases in a biological system is a respirometer. Use of a respirometer and other devices have allowed scientists to use calorimetry in order to study the physiology and heat production in various animals and plants, often in relation to energy metabolism. As yet, however, researchers have not been able to successfully use this information to screen plants for favorable genetic characteristics in particular environmental conditions. The coordination of factors such as crop yield maximization with respiratory efficiency or net photosynthesis rates in leaves, chloroplasts, or whole plants has yet to be successfully achieved. Further, the metabolic basis of genetics and environmental stress interactions also remain relatively unknown. At present there is no known standard single metabolic screening rate for determining genetic characteristics for such qualities as heat, drought, or salt tolerance among plants and plant cultivars.

It is thus highly desirable to develop a method for screening plants or plant strains which can use plant respiration so as to determine which plants are best suited for which environmental conditions. It is also desirable to have a system for metabolic testing of plants which subjects them to a wide range of various factors such as temperature, moisture, or salinity. It is further desired that such a system be able to simply and efficiently treat plants or plant parts in order to quickly and accurately detect, separate, and characterize genetic traits and genetic lines among or within plant cultivars.

SUMMARY OF THE INVENTION

In accordance with the present invention, a method is provided for screening plants for their favorable genetic characteristics under various environmental conditions through a biothermographic analysis comprising the steps of:

a. isolating a viable plant sample or part thereof;

b. placing the plant sample in a sealed apparatus wherein it is subject to a specific set of physical, chemical, biological or other environmental factors and wherein the total heat production of the sample over a given period of time can be measured;

c. subjecting the plant sample to a particular set of environmental conditions for a given period of time and measuring the total heat production of the plant sample during that period of time without affecting the viability of the plant sample;

d. repeating the above steps for at least one additional viable plant sample; and e. using the determined heat production data from the plant samples under the specific set of environmental conditions employed so as to screen the samples for favorable genetic characteristics under those environmental conditions.

The present invention can be used to asses plant viability and predict plant performance in terms of biological and economical yield or crop maturity under a variety of environmental conditions such as ranges in temperature, moisture level, salinity, toxicity, or pathogenicity. The present invention provides a total system of laboratory monitoring techniques for detection, identification, and characterization of genetic expressions practical to crop productivity and breeding. By use of the calorimetric studies in accordance with the present invention, interpretation of thermal data from test plant materials under controlled environmental conditions can be used to accurately predict how plants will react to particular conditions. The biothermographic analysis of the invention allows for treatment of whole plants as seeds, seedlings or adults, or parts thereof such as leaves, stems, or roots in order to obtain valuable information without affecting the viability of the plant. The results from this biothermographic analysis can thus be used to predict, monitor, and help increase crop production and yield. The present invention constitutes a rapid, non-destructive, repeatable test which can provide important information regarding plants in a simple and inexpensive manner unobtainable using prior art methods.

DETAILED DESCRIPTION OF THE PREFERRED EMBODIMENTS

The biothermographic analysis of the present invention can be useful in screening plants, whole crops, or plant parts for particular responses to a range of environmental conditions including but not limited to heat, cold, water saturation or dehydration, and varying levels of salinity. Ideally, the invention can be used to detect and characterize particular plants and plant strains which flourish under any given set of environmental factors. The ability of plants to cope with differing conditions can be evaluated through the measurement of that plant's dissipation of heat. Although thermographic analysis of plants has previously been conducted (see, e.g., Prat, *Can. J. Bot.* 30: 379–394 (1952)), this information has not been used in a technique by which favorable genetic characteristics under specific environmental conditions can be predicted.

During respiration, heat dissipates. In animals, dissipated heat is used to keep the body insulated against the cold. However, in plants, this dissipated heat escapes as waste thermal energy, and thus can be monitored. In the present invention, plant heat production is measured by a calorimeter or microcalorimeter nondestructively over a period of time and under a given set of environmental conditions.

Biothermography is the process of recording the heat production data and comparing it to other physical parameters, such as temperature, moisture, or size of plant, in order to identify metabolic patterns of specific plants under various conditions. The biothermographic analysis conducted in the present invention allows one to identify which plant strains will do better under certain environmental conditions, which plant strains are most tolerant to certain stressful conditions, and which crops will yield the most under field conditions in a given region.

The method of carrying out biothermographic screening of plants for favorable genetic characteristics in accordance with the present invention can be conducted using a viable plant sample or plant part. Thus, the techniques of the invention can be carried out using seeds, seedlings, leaves, stems, whole adult plants, or other viable parts thereof. In order to obtain a record of the metabolic functioning of the plant sample, it is preferably placed into a sealed apparatus capable of recording dissipated heat while the sample experiences a specific set of physical, chemical or biological conditions. A suitable apparatus is a calorimeter or microcalorimeter capable of measuring total heat production from the sample over a given period of time. To adjust the environmental conditions that the sample will experience, various devices can be used in conjunction with the calorimeter. For example, in order to alter the moisture content in the apparatus, a humidifying/dehumidifying chamber can be used in conjunction with the calorimeter. Wherein one wishes to obtain readings of dissipated heat under varying temperatures, an incubator can be used to set the temperature in the calorimeter chamber. Other parameters, such as salinity, amount of oxygen or $CO_2$ in the chamber, reaction to UV light, or reaction to toxic chemical or biological agents, can be assessed by subjecting the plant sample to different levels of a particular condition either before or during the measurement of total heat production.

In order to obtain useful information regarding the dissipated heat from the plant sample, it will be necessary to measure total heat production for a given period of time, as well as the weight of the plant sample treated. It is particularly useful to then determine a biothermal index (or B.I.) for each of the plant samples analyzed. The biothermal index will be determined by dividing the total heat production as measured per a given sample by the weight of that sample. When carrying out the present invention, the plant sample which is subject to the specific set of environmental conditions for a given period of time (such as five minutes, 10 minutes, 30 minutes, etc.) will have a total heat production which is preferably recorded in microwatts or milliwatts. Thus, the biothermal index of the present invention is preferably recorded in terms of microwatts per hundred milligrams or milliwatts per hundred grams. The heat production data as expressed in the biothermal index allows one to analyze and compare the metabolic functioning of the various plant samples so as to predict in a quick and reliable manner their ultimate performance in a given region. This will be particularly useful when carried out with regard to germinating seeds which can be nondestructively tested as to their temperature or moisture stress tolerance.

The measurement of heat production per unit weight of a viable plant sample as carried out in the present invention is utilized to assess metabolic characteristics of the sample, and is particularly useful in comparing the performance of a particular sample in a particular environment with samples from other plant cultivars in that same environment. In such a way, the method of the present invention can be utilized to screen particular plant cultivars for highest potential biological yield, seedling vigor, germplasm stability, or other desirable genetic characteristics.

The preferred method of operation is to isolate and weigh a viable plant sample, such as a five day old plant seedling, and then place that sample in a sealed apparatus wherein the total heat production of the sample can be measured, and wherein at least one environmental parameter, such as temperature, moisture level, or salinity, can be maintained at a constant level throughout the given period that the heat production is being measured. To give important comparative data on different plants, a second viable plant sample is then subjected to the same set of environmental conditions for the same period of time that the first plant sample has been subjected to. It is thus preferred for most accurate comparative data that the second plant sample utilized be similar to the first, e.g., that germinating seeds be measured against other germinating seeds. After both plant samples have been measured for heat production, a biothermal index for each of the samples is obtained which represents total heat production measured per unit weight of each sample. These steps can be carried out for an infinite number of samples or for groups of samples such as would be the case when measuring populations of plants or particular plant varieties.

The biothermographic analysis of the present invention can be used to determine plant tolerances to various conditions, indicate optimal or suboptimal conditions for specific strains of plants, and to screen plants for favorable genetic expressions such as biological or economic yield for a given environment. The biological yield of a particular plant sample or plant population refers to the ultimate yield of biomass that will be obtained for a particular plant. It has been determined that for a given set of plants measured using the method of the present invention, the plants with the lowest biothermal index will be those having the greatest potential biological yield. It is thus the case that the screening of plants for biological yield can be accomplished by carrying out measurement of heat production as indicated above, determining the biothermal index of heat production per unit weight of sample, and ranking the plant samples in terms of the determined biothermal index. In such a ranking, the samples with the lowest biothermal index will be those plant samples having the greatest potential biological yield.

It has also been determined that the favorable genetic characteristic of seedling vigor can also be screened using the biothermal index obtained in the present invention. It has been observed that plant samples having the highest biothermal index are those which will have the greatest seedling vigor. It is obvious that there will be a number of cases wherein seedling vigor will be a desirable characteristic to be determined in order to best assess or plan for uses of crops in particular environments. By carrying out the biothermographic analysis of the present invention and ranking the plant samples measured in terms of the determined biothermal index, one can select those samples which have the highest measured biothermal indices, and these will be the samples having the greatest seedling vigor.

Another useful embodiment of the present invention is the determination of a genetic baseline obtained by a linear regression analysis of the recorded data points for the biothermal index Y of a given sample and the environmental condition (such as moisture level) X. From the recorded data, a genetic baseline is obtained from the plot of X vs. Y, and a regression line $Y = aX + b$ is determined which can give useful information regarding plant reaction or resistance to specific conditions. As one example, the biothermographic test of the present invention can be used to assess the drought resistance. In such a case, the biothermal analysis of the present invention is used on plant samples under conditions wherein varying degrees of moisture are presented to each plant sample while heat production is measured.

In the preferred embodiment, plants will be tested at 3-4 levels of dehydration, e.g. no dehydration, 25% dehydration, 50% dehydration, etc. Since the tests of the invention are non-destructive, one can carry out a measurement at one level of moisture for a particular plant (e.g., at room temperature and a relative humidity of 40%), then adjust the sample to another moisture level by dehydrating the chamber to a desired level and take another reading on the same plant, and so on until all desired readings are obtained at the various moisture levels. This procedure can be carried out as well for other conditions for which tolerance or resistance to the condition is to be determined, such as heat, cold, salinity, toxins, or plant diseases.

Once the data have been received, a linear regression analysis is used to obtain the genetic baseline equation $Y = aX + b$. In the regression line analysis, the effect that the condition such as drought or low moisture has on the plant tested is indicated by the slope as determined in the genetic baseline equation. By ranking the individual plant samples or strains in terms of the slope of the genetic baseline, one can determine which of the plants were affected least by the conditions such as reduction in moisture. The biothermographic analysis of the present invention thus can be employed successfully to assess a plant or plant strain's resistance to changes in a specific environmental condition such as moisture availability, salinity, heat or cold. Further, this information can be obtained quickly, inexpensively, and under simple controlled laboratory conditions which will correlate to conditions in the field.

Additionally, the genetic baseline method can be used to accurately predict yield ratios, in the field. To carry out this test, a biothermographic procedure as described above is conducted for two separate plant samples or strains, and a genetic baseline is obtained from linear regression of a plot of Y (heat output) and X (weight of the sample). From the equation $Y = aX + b$, slope will be proportional to biological or economical yield, with lower a indicative of greater potential biological yield. In a test of wheat and triticale plants, a biothermal analysis conducted in accordance with the present invention indicated a lab ratio of 100:169 (wheat: triticale) in terms of slope a from the genetic baseline measures for each plant. This was indicative of the potential biological yield for each plant, with the triticale variety expected to have the greater yield due to a *lower* determined slope a. In field tests, a yield ratio of 5 lines of each plant recorded an actual wheat: triticale ratio of 100:162, thus confirming that the genetic baseline analysis of the biothermographic method of the present invention could also be used to predict crop yield. In the genetic baseline equation as conducted above, the element b will be directly proportional to seedling vigor, and relative seedling vigor can also be determined from the direct reading of b in the equation.

Using the present invention, one can also measure populations or groups of plant germplasm samples so as to measure for the favorable genetic characteristic of germplasm stability. In this case, the populations or groups of plants undergo repeated biothermal analysis as indicated above. In this case, the total measured heat production versus weight of the sample is plotted on a graph for both the parent plant and its germplasm samples. A genetic base line is obtained from a linear regression analysis of each germplasm and the corresponding correlation coefficient between parent plant and germplasm is obtained. In a genetic base line wherein $Y =$ heat output and $X =$ weight, the equation $Y = a X + b$ can be obtained in which slope a represents yield potential while Y-intercept b represents seedling vigor. The correlation coefficient (R) obtained from these genetic base lines thus will represent germplasm stability, purity or homogeneity. When the correlation coefficient (R) is closet to 1, the highest stability between parent plant and germplasm is achieved. Those populations or groups of plants closest to a correlation coefficient of 1 will thus be those having the greatest germplasm stability.

The biothermographic techniques as provided in the present invention can also be used to predict crop maturity and optimal harvest time of particular plants. This particular technique will be extremely important in determining optimal planting time for particular crops. The screening method of the present invention is carried out by first obtaining a biothermal index as described above for a particular plant sample under a particular set of environmental conditions. Next, a linear regression line is plotted using the Y variable of biothermal index and the X variable as time from original planting. The maturity harvest index is obtained from the linear regression line by calculating variable X when Y approaches O on the assumption of projected maximal yield. The crop maturity time and optimal harvest time can thus be predicted using the maturity harvest index.

In carrying out the method of the present invention, it is generally contemplated that the method will be used to analyze one individual plant as a whole plant at one time in a nondestructive testing period totalling no more than about 30 minutes in length. The whole plant preferably at the age of anywhere from about 3 to 10 days is collected, weighed and sterilized by surface dripping or spraying with solutions such as hypochloride or ethanol. Before placing the plant in a microcalorimeter, the plant should be blotted dry of solution. For testing at a particular level of temperature, temperature equilibrium is allowed to be achieved for the microcalorimeter chamber. This often takes no more than about 10 minutes. During the next 10 minute period, the sample is then analyzed for total heat production. The instrument used in the present invention is preferably a sealed twin-cell type of microcalorimeter, having four channels with preset temperature constant with a variation of no more than about 0.005° C. The total turnaround time to prepare the chamber for a second individual plant to be analyzed is generally around thirty minutes. After the heat production of the plant is measured, data can be recorded, computed and correlated, statistically treated, and interpreted. The analysis of the present invention is rapid, non-destructive, and cost effective. The present method is a quick and efficient way of determining important genetic characteristics of plants at low cost which can be used for the general benefit of crop and plant management.

The following examples are presented as illustrative of the present invention and are not intended to limit its scope in any way:

EXAMPLE 1

As an example of carrying out the biothermographic analysis of the present invention, a population of commercial mungbeam seeds was soaked in distilled water overnight at 25° C., and were allowed to germinate at a temperature under 20° C. After 3 days, heat production was obtained by sealing the plants individually in a microcalorimeter which was set at a temperature of 20° C. The total dissipated heat was measured for a period of 15 minutes. The heat production data were recorded along with the weights of the germinating seeds at the time the measurements were taken. The results of these tests are presented in Table 1.

TABLE 1

| Sample | Weight (mg) | Heat Production (microwatts) | Biothermal Index (mWatts/100 g) |
|---|---|---|---|
| 1. | 226 | 220 | 97.3 |
| 2. | 206 | 204 | 99.0 |
| 3. | 216 | 189 | 87.5 |
| 4. | 197 | 208 | 105.1 |
| 5. | 231 | 207 | 89.6 |
| Mean | 215 | 205 | 95.7 |
| S.D. % | 6.4 | 6.1 | 7.4 |

After obtaining the heat production data, a biothermal index (or B.I.) was determined as the heat production per unit weight of each sample. In this case, the B.I. was recorded in milliwatts per 100 grams. The results for five germinating seeds can be observed in Table 1. The measurements for the five plants tested were then averaged to give a mean B.I. for the plant population studied. This testing procedure is the standard method for obtaining the biothermal data in accordance with the invention which is useful in assessing metabolic characteristics or multigenetic features of plants in a specific environment.

EXAMPLE 2

The biothermographic analysis of the present invention is used in a determination of the genetic characteristic of biological yield. In this aspect of the invention, screening of alfalfa cultivars has been accomplished quickly and efficiently in a manner that will enable one to accurately predict the ultimate biological yield of the cultivars in the field.

For the experimental procedures, three varieties of alfalfa plants were tested in the laboratory for their heat production at temperatures of 20° C. and 30° C. In these procedures, 4-day old whole alfalfa plants of the "EGY", "CAL" and "N.Z." varieties were collected, weighed, and sterilized by spraying with hypochlorite or ethanol solution and blotted dry. The microcalorimeter chamber was prepared by setting the temperature at either 20° C. or 30° C., and allowing the chamber to achieve equilibrium (usually about 10-15 minutes). The samples were then measured for heat production at 20° C. or 30° C. for a period of 10 minutes. The total heat production was measured, and a biothermal index (or BI) was obtained for each of the plant varieties at the two temperatures. The recorded data from this test is presented at Table 2A.

TABLE 2A

| Biothermographic Test on Germplasmic plants of alfalfa cultivars | | | |
|---|---|---|---|
| | Energy Output, mWatts/100 g (4th Day) | | Productivity |
| Variety | 20° C. | 30° C. | Rating |
| EGY | 93 | 71 | 1 |
| CAL | 103 | 83 | 2 |
| N.Z. | 108 | 100 | 3 |

In Table 2A, the plant varieties were ranked in terms of observed BI values in terms of milliwatts per 100g. As can be seen in the Table, the variety with the lowest BI has been accorded the highest productivity rating, and vice versa. It was thus predicted that the EGY variety would have the greatest biological yield, followed by the CAL variety and then the N.Z. variety. Field tests were subsequently carried out to assess the actual productivities of each variety when allowed to grow under normal conditions. The actual harvest production in terms of kg per 6m² plot was recorded, and this data is presented in Table 2B.

TABLE 2B

| Field Variety Test on alfalfa cultivars. | | | |
|---|---|---|---|
| | Production (Av. Kg/6 M² plot)* | | |
| Variety | Annual Harvest (13 Cuts) | Warm Months (8 Cuts) | Cool Months (5 Cuts) |
| EGY | 22.95 (100)** | 15.56 (100) | 7.39 (100) |
| CAL | 20.26 (88) | 14.41 (92) | 5.85 (75) |
| N.Z. | 16.81 (73) | 12.73 (82) | 4.18 (55) |
| x | 20.01 | 14.23 | 5.81 |
| C.V. % | 1.1 | 10.4 | 28.9 |

*Values × 1.67 = Ton/Hectare.
**Parenthesis indicate normalized production for comparison.

The ranking of the plants based on low-to-high B.I. values accurately predicted the resulting productivity of the alfalfa varieties in the wild. Harvests under both the warmer months and the cooler months confirmed the prediction that the EGY variety would be most productive, followed by the CAL and the N.Z. varieties. It was also predicted by the tests that this difference in the productivity would be observed during both warmer and colder month conditions, since the ranking of the varieties stayed constant at both the temperatures tested, 20° C. and 30° C. By use of the techniques of the present invention, one can use the biothermographic tests to predict actual biological harvest yield in the wild.

EXAMPLE 3

The biothermographic analysis of the present invention was used to test drought resistance in plants. In the experiment, a winter variety of wheat, *Yecora rojo*, was used in an assessment of heat production at various levels of dehydration. Tests were carried out on 4 adult wheat plants, and the data were recorded, as indicated in Tables 3A-B. The plants were placed in microcalorimeter chambers at specific levels of humidity, followed by tests at decreasing levels of moisture (by dehydrating the chamber). The plants were initially tested at a relative humidity of 40% at room temperature. The plant moisture level was gradually adjusted so that each plant was measured at decreasing levels of moisture in increments of 10% dehydration. Testing thus occurred at dehydration levels of 10%, 20%, 30% and finally 40%. The measured biothermal index (or B.I.) at each of the moisture levels is observed in Table 3A. As can be seen in Table 3A, the measured B.I. increased with increasing dehydration levels.

TABLE 3

GERMPLASMIC SCREENING DATA ON WHEAT
(Variety: *Yecora rojo*) FOR DROUGHT RESISTANCE Table 3A.
BIOTHERMOGRAPHY TEST VALUES (mWatts/100 g)

| % Dehydration (Whole Plant) | B. I. (mWatts/100 g) (Y) Plant # | | | |
|---|---|---|---|---|
| | 1 | 2 | 3 | 4 |
| 0 | 153 | 162 | 106 | 118 |
| 10 | 184 | 196 | 118 | 127 |
| 20 | 208 | 208 | 127 | 130 |
| 30 | 222 | 221 | 141 | 136 |
| 40 | — | — | — | — |

Table 3B Drought Resistance Rankings

| Plant # | Regression Line | Corr. Coef. | Drought Resist. Ranking No. |
|---|---|---|---|
| 1 | Y = 1.78 X + 162 | R = 0.949 | 3 |
| 2 | Y = 1.89 X + 168 | R = 0.964 | 4 |
| 3 | Y = 1.14 X + 106 | R = 0.997 | 2 |
| 4 | Y = 0.51 X + 124 | R = 0.982 | 1 |

The recorded data for the four plant samples were plotted as B.I. (Y) vs. relative humidity (X), and a linear regression line of the equation $Y = aX + b$ was obtained for each sample. The linear regression line data can be observed in Table 3B. Based on this table, a drought resistance ranking number was given to each plant sample based on the slope of the regression line. The regression line slopes correspond to the effect of the dehydration condition on the plants, and the plants best able to handle drought conditions were those which had minimal changes to their measured B.I. as reflected in the slope of the regression line. The drought resistance as reflected in the rankings was confirmed in actual field tests results. Thus, the resistance to change in measured B.I. under increasing conditions of dehydrated can be used to predict drought resistance of plant strains under natural conditions.

EXAMPLE 4

The biothermographic analysis of the present invention can be used to screen plant populations for the characteristic of genetic purity or stability. In such a test, plants and their germplasm samples are analyzed using the biothermographic tests as described above. The test was conducted using rice varieties starting with a local variety Hassawai, an original local rice strain with relatively low yield, 2-2.5 ton per hectare. Through field selection, a second rice variety, Hassa No. 1, was observed to have an increased yield on harvest. Later, Hassa No. 1 was crossed with varieties known as Hassa H39 and Hassa H40 to obtain even better yields. A biothermal analysis was carried out on 3-4 day old plants in all test sample populations, and the results of these tests are observed in Table 4.

TABLE 4

BIOTHERMOGRAPHY TEST ON RICE BREEDING LINES FOR GENETIC BASELINE STANDARDIZATION AND MANAGEMENT

| Rice Lines Breeding | Genetic Baseline* Y = a (X) + b | (R)** | Est Field/Yield tons/hectare |
|---|---|---|---|
| Hassawai, Local | Y = 2.4 X + 25 | 0.968 | 2-2.5 |
| Hassa No. 1 | Y = 1.7 X + 90 | 0.841 | 3-3.5 |
| Hassa No. 1XH39 | Y = 1.6 X + 86 | 0.863 | 4-4.5 |
| Hassa No. 1XH40 | Y = 0.8 X − 13 | 0.801 | 6-6.5 |

*at 27° C. where (Y) = Heat Output and (X) = Weight; and (a) = Yield potential and (b) = Seedling Vigor.
**Correlation Coefficient (R) = Line purity and/or Cultivar stability.

In this experiment, a genetic baseline for the rice varieties was constructed wherein Y = total heat output, and X = weight of the samples, giving on linear regression analysis an equation of $Y = a(x) + b$. The genetic baseline was constructed for each variety, and a corresponding correlation coefficient (R) was obtained for each germplasm sample. In the genetic baseline of this test, $Y = a(x) + b$, slope a represents yield potential and Y-intercept b represents seedling vigor. The correlation coefficient R represents germplasm purity, homogeneity or stability with the strains closest to a coefficient R of 1 being those with the highest germplasm stability. As in the above examples, the smallest a value also notes the highest yield.

EXAMPLE 5

An experiment was conducted on wheat and triticale plants to exhibit how the biothermographic analysis of heat production could be used to predict harvest yield in particular plant species. In this case, five lines of wheat (Westbred variety) were tested against five lines of a wheat-rye hybrid (Triticale variety) using the principles of the biothermographic analysis discussed above. The heat production data was recorded and a genetic baseline was constructed using as the Y-axis heat output, and weight of the sample as the X-axis. A genetic baseline based on linear regression was obtained for these results in an equation of $Y = a(x) + b$, as indicated in Table 5. Under this experiment, the slope a was indicative of potential yield with the lower value of a being indicative of a higher potential yield.

TABLE 5

BIOTHERMOGRAPHY TEST ON WHEAT AND TRITICALE FOR GENETIC BASELINE YIELD COMPARISON VS. FIELD DATA

| By Biothermography Test (Y) = a (X) + b (a = Yield and b = Seedling Vigor) | Predicted Yield Ratio | |
|---|---|---|
| Wheat Var. = Westbred (Y) = 2.2 (X) + 27 | $(R)_5 = 0.551$ | 100 |
| Wheat-Rye = Triticale (Y) = 1.3 (X) + 269 | $(R)_5 = 0.355$ | 169 |

By Field Harvest Spikes, 5 Lines Composite (g.)*

Wheat Var. = Westbred Lines: 115, 119, 201, 188, 197;
Wt. = 7.75, 7.08, 6.31, 5.99, 4.19
Mean Wt. (g) Dry Matter = 6.25; S.D. % 23
Wheat-Rye = Triticale Lines: 169, 198, 126, 105, 114
Wt. = 12.86, 11.15, 10.21, 9.18, 7.34
Mean wt. (g) Dry Matter - 10.15; S.D. % 22

TABLE 5-continued

Actual Yield Ratio, Wheat:wheat-rye = 100:162

The results of the biothermography test indicated that the triticale should outperform the wheat in terms of yield by a ratio of 169:100, as indicated in Table 5. Field tests later confirmed this prediction. When wheat and triticale were actually grown and harvested in the wild, the resulting yield was observed to favor triticale by a ratio of 162:100, thus confirming the prediction of the biothermal analysis as indicated in Table 5.

EXAMPLE 6

An alternative use of the genetic baseline method of the biothermographic analysis of the present invention is to employ the readings for predicting crop maturity/-harvest time which will aid in overall management capability regarding particular plant crops. In this embodiment, readings of heat production are obtained from plants, a biothermal index is obtained, and a linear regression line is plotted using the Y variable as biothermal index and the X variable as the time. Experiments were conducted in this regard using the biothermal analysis discussed above with respect to potato buddings and grass forage plantlets. The information received revealed important trends regarding genetic potential and variation for early harvest of crops, as indicated in Tables 6A and 6B.

TABLE 6A

BIOTHERMOGRAPHY TEST ON POTATO BUDDINGS FOR MATURITY HARVEST INDEX VIA GENETIC BASELINE METHOD

| Temp. Effect | Genetic Baseline* | (R)** | M.H. Index*** |
|---|---|---|---|
| 12° C. | Y = −36 X + 296 | −0.973 | 8.3 |
| 27° C. (Local var.) | Y = −88 X + 402 | −0.875 | 4.6 |

*Y = Biothermal Index, and X = Age
**R = Correlation Coefficient
***M.H. Index was derived from the Genetic Baseline variable X when Y value approaching to zero at maximal projected yield.

TABLE 6B

BIOTHERMOGRAPHY TEST ON GRASS GERMPLASMIC PLANTS FOR MATURITY HARVEST INDEX VIA GENETIC BASELINE

| Grass Var. | Genetic Baseline* | (R)** | M.H. Index |
|---|---|---|---|
| O W P | Y = −62 X + 581 | −0.982 | 9.3 |
| L G | Y = −47 X + 461 | −0.785 | 9.8 |
| R W | Y = −41 X + 537 | −0.892 | 13.3 |
| S G | Y = −25 X + 443 | −0.741 | 17.5 |

*Y = Biothermal Index, and X = Age
**R = Correlation Coefficient
***M.H. Index was derived from the Genetic Baseline variable X when Y value approaching to zero at maximal projected yield.

In Table 6A, the genetic baseline information obtained on a local potato variety tested under temperatures of 12° C. and 27° C. is presented. The tests reveal that the effect of temperature will be important in deciding ultimate harvest maturity time, as indicated in the Maturity Harvest index. The Maturity-Harvest (or M.H.) index was calculated on variable X (time, in days or months for various crops) when Y approaches zero on the assumption of projected maximal yield. In these tests, it was concluded from the M.H. index that the local variety of potato plants favored a warmer temperature, and that at 27° C. avg. temperature, this variety would be ready for harvest at about half of the time required for planting at 12° C., or approximately 4.6 months vs. 8.3 months under this test.

Table 6B illustrates another experiment of M-H index using four different grass cultivars. In this experiment, as above in the potato plant example, biothermal readings were taken for the four grass varieties, and genetic baseline measurements were analyzed to produce the M-H index. The maturity harvest index showed that the varieties of OWP and LG would reach maximum harvest potential at an earlier time than would varieties RW and SG.

What is claimed is:

1. A method of biothermographically screening plants for seedling vigor under a specific set of environmental conditions comprising the steps of:
   a. isolating and weighing a viable plant sample comprising a plant at any life stage or a viable part thereof;
   b. placing the plant sample in a sealed apparatus wherein the sample can be subjected to a specific set of physical, chemical or biological conditions and wherein the total heat production from the sample over a given period of time can be measured, without affecting the viability of the plant sample;
   c. subjecting the plant sample in the apparatus to a specific set of physical, chemical or biological conditions for a given period of time and measuring the total heat production of the plant sample during that given period of time without affecting the viability of the plant sample;
   d. repeating the above steps for at least one additional viable plant sample;
   e. using the measured heat production of the weighed plant samples under the given set of conditions so as to screen the samples for seedling vigor under that set of conditions;
   f. determining a biothermal index for each of said plant samples by dividing the total heat production measured per sample by weight of the sample; and
   g. ranking the plant samples in terms of the determined biothermal index, and selecting those samples with the highest biothermal index as those having the greatest seedling vigor.

2. A method of biothermographically screening plants so as to predict optimal harvest time comprising the steps of:
   a. isolating and weighing a viable plant sample comprising a plant at any life stage or a viable part thereof;
   b. placing the plant sample in a sealed apparatus wherein the sample can be subjected to a specific set of physical, chemical or biological conditions and wherein the total heat production from the sample over a given period of time can be measured without affecting the viability of the plant sample;
   c. subjecting the plant sample in the apparatus to a specific set of physical, chemical or biological conditions for a given period of time and measuring the total heat production of the plant sample during that given period of time, without affecting the viability of the plant sample;
   d. determining a biothermal index for the plant sample over the given period of time by dividing the total heat production measured by the weight of the sample;

e. generating a linear regression line using as one variable the measured biothermal index and using age of the plant sample as the other variable; and f. determining an optimal harvest time using the calculated linear regression line by calculating the age variable when the variable representing the measured biothermal index approaches zero.

3. A method according to claim 2 further comprising the steps of:

g. repeating the above steps for at least one additional viable plant sample; and h. comparing the determined optimal harvest time of the two plant samples so as to obtain a measurement of the relative optimal harvest time of the two plant samples.

4. A method of biothermographically screening plants for the favorable genetic characteristic of germplasm stability under a specific set of environmental conditions comprising the steps of:

a. isolating and weighing at least one viable parent plant sample comprising a parent plant at a life stage where it produces germplasm;

b. placing the parent plant sample in a sealed apparatus wherein the sample can be subject to a specific set of physical, chemical or biological conditions and wherein the total heat production from the sample over a given period of time can be measured without affecting the viability of the plant sample;

c. subjecting the parent plant sample in the apparatus to a specific set of physical, chemical or biological conditions for a given period of time and measuring the total heat production of the plant sample during that given period of time without affecting the viability of plant sample;

d. repeating the above steps for at least one viable plant germplasm sample comprising a plant germplasm obtained from the parent plant sample;

e. generating a linear regression line from a plot of the total heat production versus weight of both the parent plant sample and the plant germplasm sample;

f. repeating the above steps for at least one additional viable parent plant sample and at least one additional viable plant germplasm sample obtained from the additional viable parent plant sample;

g. obtaining a correlation coefficient for each linear regression line generated for each parent plant-plant germplasm set;

h. ranking each parent plant-plant germplasm sample set in terms of the obtained correlation coefficients and i. selecting the set of parent plant-plant germplasm samples having a correlation coefficient closest to 1.0 as those with the greatest germplasm stability.

* * * * *